United States Patent [19]

Okano et al.

[11] Patent Number: 4,705,895
[45] Date of Patent: Nov. 10, 1987

[54] 5,5'-DIAMINO OR 5,5'-DIACETAMIDO-2,2'-BIS(DIPHENYL-PHOSPHINO)-1,1'-BINAPHTHYLS

[75] Inventors: Tamon Okano, Canberra, Australia; Hidenori Kumobayashi; Susumu Akutagawa, both of Kanagawa, Japan; Jitsuo Kiji, Tottori, Japan; Hisatoshi Konishi, Tottori, Japan; Keiichi Fukuyama, Tottori, Japan; Yasunobu Shimano, Okayama, Japan

[73] Assignee: Takasago Perfumery Co., Ltd., Tokyo, Japan

[21] Appl. No.: 937,805

[22] Filed: Nov. 21, 1986

[30] Foreign Application Priority Data

Feb. 1, 1986 [JP] Japan ................................. 61-19203

[51] Int. Cl.$^4$ ............................................. C07F 9/50
[52] U.S. Cl. .......................................... 564/15; 556/22
[58] Field of Search ............................................. 564/15

[56] References Cited

U.S. PATENT DOCUMENTS 4,564,708 1/1986 Yagi et al. ............................... 568/14
4,605,750 8/1986 Kumobayashi et al. .................. 556/7

Primary Examiner—Anton H. Sutto
Attorney, Agent, or Firm—Sughrue, Mion, Zinn, Macpeak, and Seas

[57] ABSTRACT

A phosphine compound represented by formula:

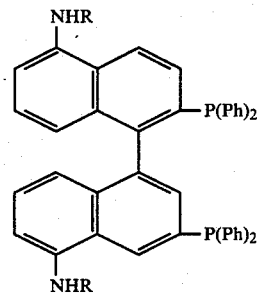

wherein R represents a hydrogen atom or an acetyl group; and Ph represents a phenyl group. The phosphine compound is capable of forming a complex with a metallic element, e.g., rhodium, ruthenium, palladium, etc., which exhibits high performances as a catalyst for asymmetric syntheses.

1 Claim, 3 Drawing Figures

5,5'-DIAMINO OR 5,5'-DIACETAMIDO-2,2'-BIS(DIPHENYLPHOS-PHINO)-1,1'-BINAPHTHYLS

FIELD OF THE INVENTION

This invention relates to a novel phosphine compounds forming a complex with a metallic element, e.g., rhodium, ruthenium, palladium, etc., which is useful as a catalyst for asymmetric synthesis.

BACKGROUND OF THE INVENTION

Many of complexes in which a chiral tertiary phosphine is coordinated to a metallic element, e.g., rhodium, ruthenium, palladium, etc., exhibit excellent performances as catalysts for asymmetric syntheses. In an attempt of improving catalytic performances of these metal-phosphine complexes, a number of phosphine compounds having special structures have hitherto been developed as recited, e.g., in Nihon Kagakukai (ed.), *Kagaku Sosetsu,* Vol. 32, pp. 237–238, "Yuki Kinzoku Sakutai no Kagaku" (1982), *Synthesis (Reviews),* pp. 85–116 (1981), etc.

2,2'-Bis(diphenylphosphino)-1,1'-binaphthyl (hereinafter abbreviated as BINAP) disclosed in U.S. Pat. Nos. 4,564,708 and 4,605,750, and Japanese Patent Application (OPI) No. 61937/80 (the term "OPI" as used herein meaning "unexamined published application") is one of the excellent phosphine compounds so far developed. However, the above described Japanese patent application referrs to substituted BINAP only by citing some examples of 3,3'-substituted BINAP.

Further, none of the conventionally proposed phosphine compounds is capable of providing catalysts which fully satisfy the requirements of selectivity, conversion, and duration in asymmetric syntheses. It has been, therefore, keenly demanded to develop a phosphine compound providing catalysts for asymmetric syntheses that exhibit markedly improved catalytic performances over the conventional ones.

The inventors previously studied aiming at development of phosphine compounds forming satisfactory catalysts for asymmetric synthesis, and found p-tolyl BINAP, i.e., (2,2'-bis(di-p-tolylphosphino)-1,1'-binaphthyl, as disclosed in U.S. Pat. No. 4,604,474 (corresponding to Japanese Patent Application (OPI) No. 199898/85).

SUMMARY OF THE INVENTION

As a result of extended researches on various BINAP derivatives, it has now been found that BINAP having an amino group or an acetamido group at the 5,5'-positions of the naphthyl ring thereof provides a metal complex having a markedly increased conversion in asymmetric syntheses as compared with unsubstituted BINAP. The present invention has been completed based on this finding.

The present invention relates to novel phosphine compounds represented by formula (I) shown below; i.e., 5,5'-diamino-2,2'-bis(diphenylphosphino)-1,1'-binaphthyl and 5,5'-diacetamido-2,2'-bis(diphenylphosphino)-1,1'-binaphthyl.

Formula (I) is represented by:

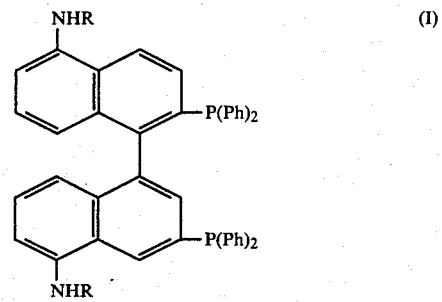

wherein R represents a hydrogen atom or an acetyl group; and Ph represents a phenyl group.

BRIEF DESCRIPTION OF ACCOMPANYING DRAWINGS

DETAILED DESCRIPTION OF THE INVENTION

Figure 1:
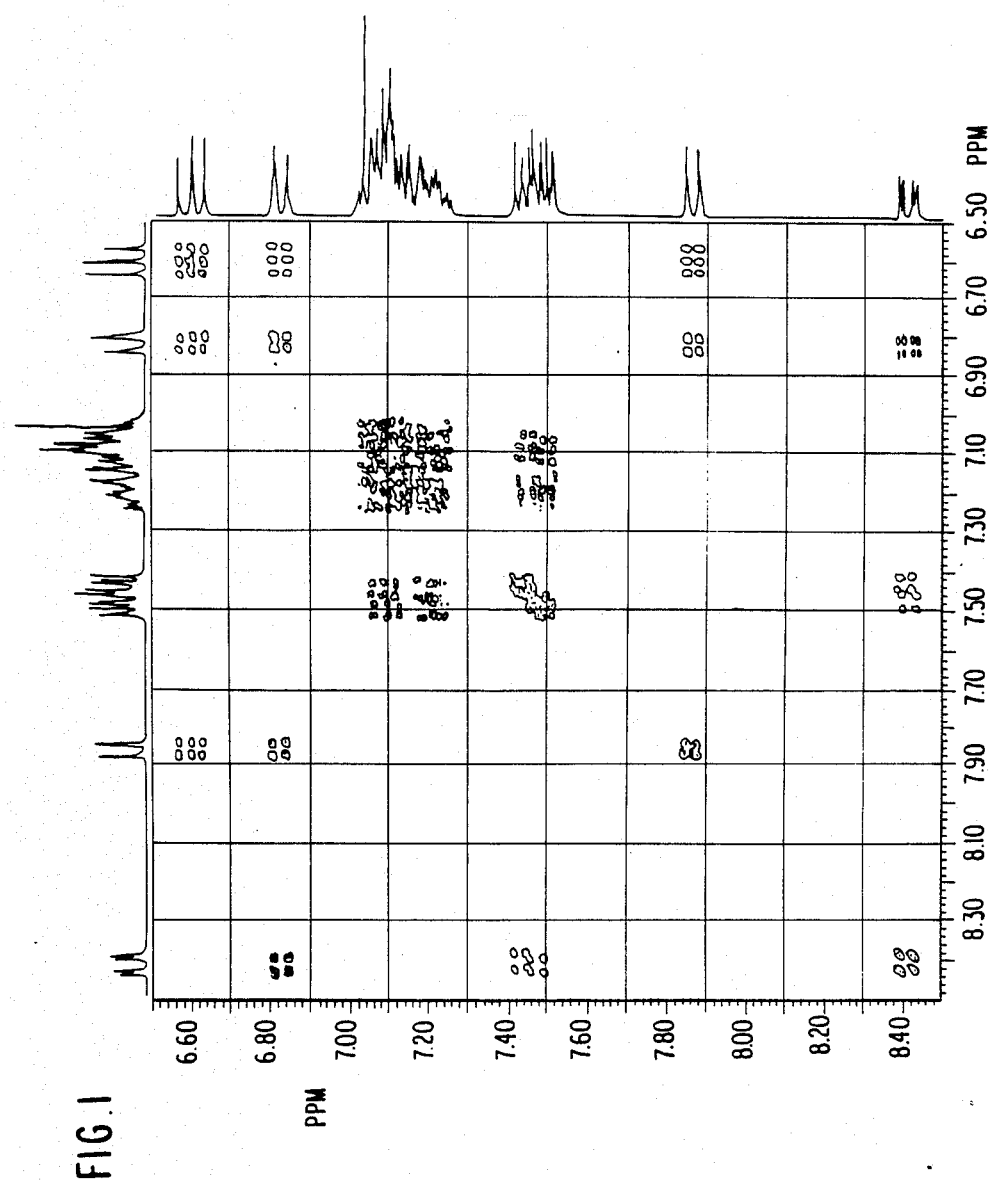
FIG. 1 is a two-dimensional NMR chart of (+)-5,5'-dinitro BINAP dioxide.

The phosphine compounds represented by formula (I) according to the present invention can be prepared from BINAP dioxide represented by formula (II) through the following reaction scheme:

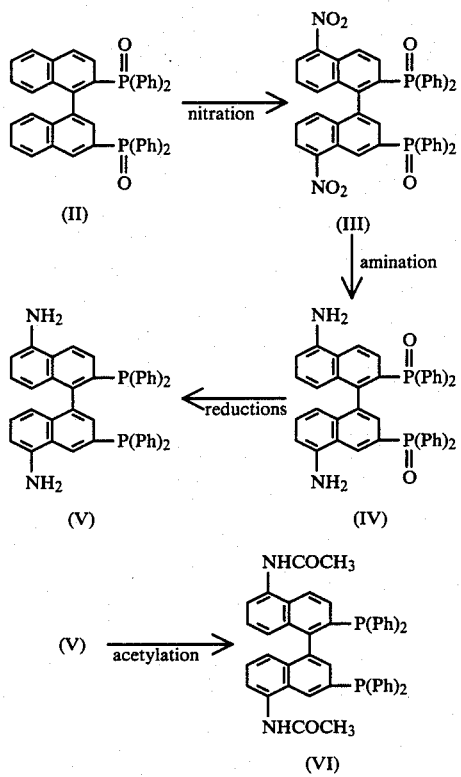

The BINAP dioxide of formula (II) can be synthesized by the process according to U.S. Pat. No. 4,564,708 (corresponding to Japanese Patent Application (OPI) No. 157094/84) which comprises reacting bromine and 1,1'-bis-2-naphthol using triphenyl phosphine as a reaction auxiliary, reacting the resulting 2,2'-dibromo-1,1'-binaphthyl with chlorodiphenyl phosphine in the presence of t-butyl lithium to form BINAP, and oxidizing BINAP with peracetic acid or hydrogen peroxide.

The BINAP dioxide (II) is reacted with an appropriate nitrating agent, such as a combination of nitric acid and acetic anhydride, to introduce a nitro group to the 5,5'-positions of the naphthyl ring thereof to give 5,5'-dinitro BINAP dioxide of formula (III). Nitration at the 5,5'-positions may be confirmed by the X-ray analysis and two-dimensional NMR analysis. The nitro groups of the compound (III) are then converted to amino groups by reduction, such as acidic reduction using stannous chloride, to form 5,5'-diamino BINAP dioxide of formula (IV). The compound (IV) is reduced with trichlorosilane ($HSiCl_3$) in accordance with a known process (see *Chem. Ber.*, Vol. 98, p. 171 (1965)) to thereby obtain the phosphine compound of formula (V) according to the present invention. The phosphine compound of formula (VI) according to the present invention can be obtained by acetylating the compound of formula (V) in a usual manner.

The phosphine compound according to the present invention is capable of forming a complex with a metallic element, e.g., rhodium, ruthenium, palladium, etc. For example, it easily reacts with a known rhodium compound, $[Rh(nbd)_2]ClO_4$ wherein nbd represents norbornadiene, to form a complex, $[Rh(5,5'\text{-amino or acetamido BINAP(nbd)}]^+ClO_4^-$.

These phosphine-metal complexes are usually employed as produced, or may be supported on a carrier, such as crosslinked polystyrene, etc.

This invention will now be illustrated in greater detail with reference to the following examples and comparative examples, but it should be understood that the present invention is not limited thereto. In these examples, all the percentages are given by weight unless otherwise indicated.

EXAMPLE 1

Synthesis of (+)-5,5'-Dinitro BINAP Dioxide

In 500 ml-volume flask was charged 180 ml of acetic anhydride, and 30 ml of 69% nitric acid was added dropwise thereto with stirring over a period of 1 hour while cooling with ice and sodium chloride. To the mixture was added dropwise 3 ml of 95% sulfuric acid. To the resulting system was further added 9.8 g (15 mM) of (+)-BINAP dioxide, followed by stirring at 0° C. for 2 hours to complete the reaction. The reaction mixture was slowly poured into 800 ml of a 10% sodium hydroxide aqueous solution cooled in an ice-water bath, followed by allowing to stand for 1 hour in the ice-water bath. The thus formed precipitate was collected by filtration, dried at room temperature under reduced pressure for 3 hours, and dissolved in a mixture of 90 ml of tetrahydrofuran (THF) and 10 ml of water. The THF was removed from the solution by evaporating on a hot water bath at 60° C., and 40 ml of THF was then added thereto while stirring to yield 11.0 g (98.6%) of the titled compount as yellow particulate crystals.

Melting Point: 340° C. or more

Elementary Analysis: Calcd. (%): C 70.96, H 4.03, N 3.76; Found (%): C 70.46, H 4.14, N 3.74

It was confirmed by the X-ray and two-dimensional NMR analyses that the product had a nitro group at the 5- and 5'-positions of the naphthyl ring. The two-dimensional NMR chart of this compound as measured by means of AM250 (an NMR spectrometer manufactured by Bruker) is shown in FIG. 1.

Synthesis of (+)-5,5'-Diamino DINAP Dioxide

A one liter-volume flask was charged with 2.21 g (3 mM) of (+)-5,5'-dinitro BINAP dioxide as prepared above and 75 ml of ethanol. To the mixture was added dropwise 192 ml of 12.1N hydrochloric acid over a period of 1 hour. A solution of 39.7 (176 mM) of stannous chloride ($SnCl_2.2H_2O$) in 45 ml of ethanol was then added dropwise to the mixture, followed by refluxing for 15 hours to complete the reaction. The reaction mixture was concentrated until a hydrochloride was precipitated. After allowing the concentrate to stand at room temperature overnight, the hydrochloride was removed by filtration. The filtrate was dissolved in 200 ml of ethanol, and the solution was neutralized with 16 ml of a 10% sodium hydroxide aqueous solution, followed by concentration. The concentrate was extracted with 50 ml of methylene chloride, and the extract was concentrated in dryness. The resulting solid was dissolved in 20 ml of hot alcohol. After cooling, 20 ml of n-hexane was added thereto to give 1.75 g (85.3%) of the titled compound as brown quartz-like crystals.

Melting Point: 340° C. or more

Elementary Analysis: Calcd. (%): C 77.19, H 4.97, N 4.09; Found (%): C 77.28, H 5.02, N 3.83

Synthesis of (+)-5,5'-Diamino BINAP

In a 200 ml-volume flask was placed 75 ml of toluene, and 12 ml (0.12M) of trichlorosilane and 23 ml (0.12M) of tri-n-propylamine were added thereto under a nitrogen stream, followed by stirring for 10 minutes. To the mixture was added 4.2 g (6 mM) of the (+)-5,5'-diamino BINAP dioxide as above prepared, followed by refluxing for 5 hours. The reaction mixture was poured into 400 ml of a 10% sodium hydroxide aqueous solution cooled with ice-water, and the mixture was extracted with 300 ml of toluene. The extract was concentrated to dryness, and the solid was dissolved in 50 ml of hot toluene. Upon allowing the solution to stand at room temperature, 2.76 g (70.5%) of the titled compound was obtained as brown particulate crystals.

Melting Point: 340° C. or more

Elementary Analysis: Calcd. (%): C 80.98, H 5.21, N 4.29; Found (%): C 81.14, H 5.35, N 4.01

Figure 2:
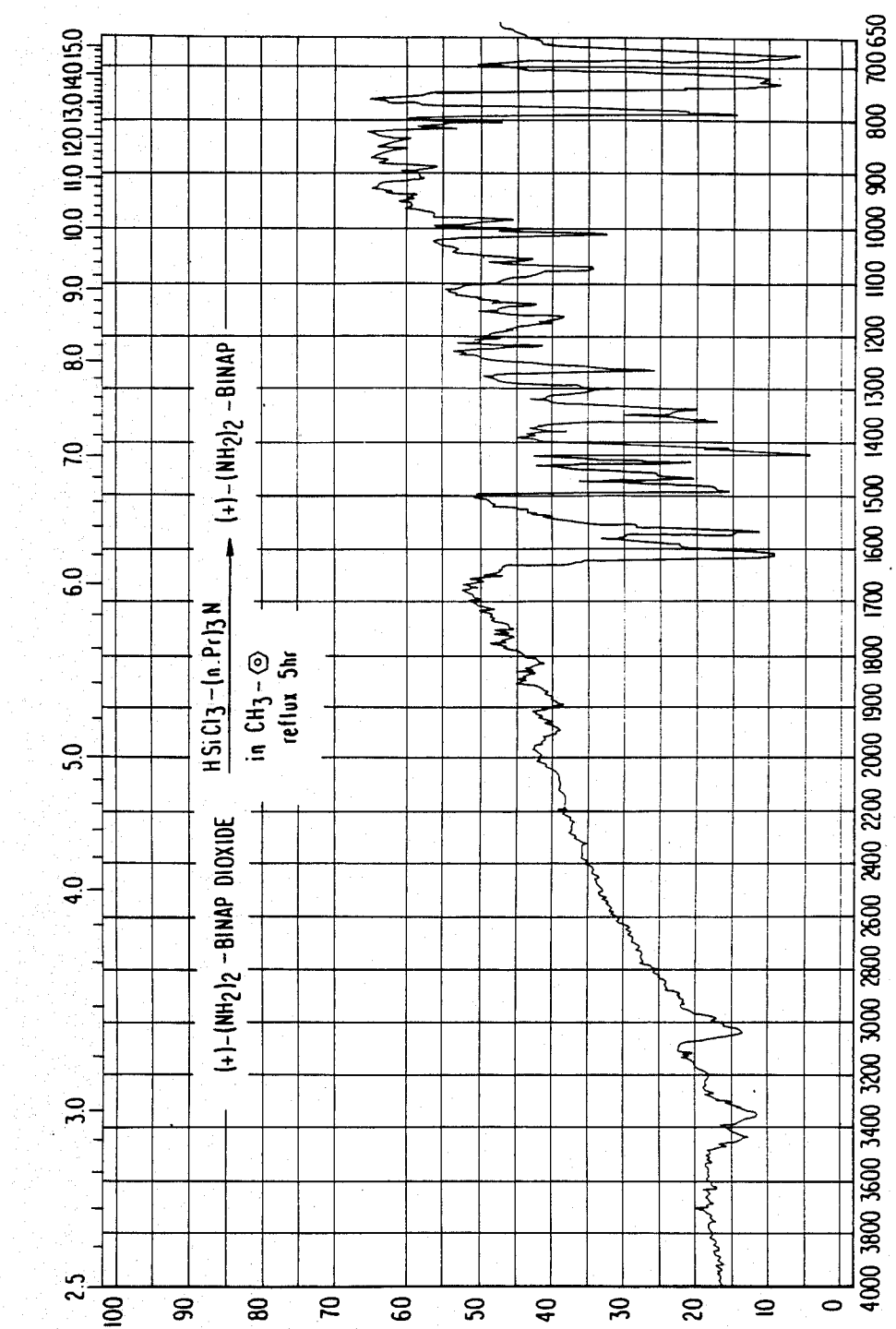
FIG. 2 is an infrared absorption spectrum of (+)-5,5'-diamino BINAP.
Figure 3:
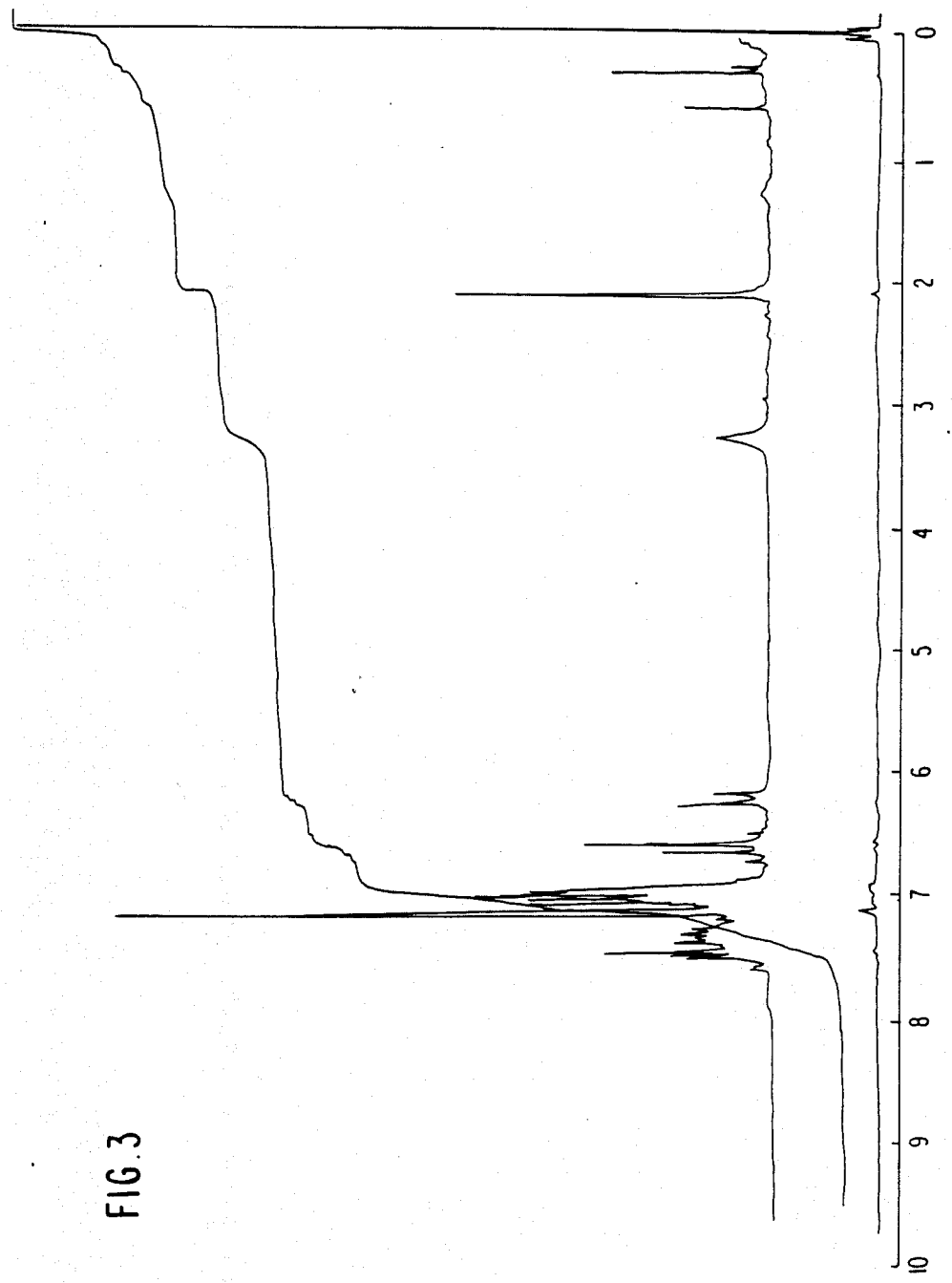
FIG. 3 is a two-dimensional NMR chart of (+)-5,5'-diamino BINAP.

The infrared absorption spectrum (KBr) and NMR chart of this compound are shown in FIGS. 2 and 3, respectively.

EXAMPLE 2

Synthesis of (+)-5,5'-Diacetamido BINAP

A 50 ml-volume flask was charged with 1.3 g (2 mM) of the (+)-5,5'-diamino BINAP as obtained in Example 1, 12 ml of acetic anhydride, and 3 ml of tri-n-propylamine, and the mixture was refluxed for 1.5 hours under a nitrogen stream. The reacton mixture was poured into ice-water, and the thus formed crystals were collected by filtration. Recrystallization from hot methanol gave 1.12 g (76.0%) of the titled compound as yellow particulate crystals.

Melting Point: 176°–178° C.

Elementary Analysis: Calcd. (%): C 78,26, H 5.16, N 3.80; Found (%): C 78.71, H 5.23, N 3.72

USE EXAMPLE 1

Preparation of [Rh((+)-5,5'-Diamino BINAP)(nbd)]+ClO4−

One milliliter of a 0.02 mM/ml solution of [Rh(nbd)2]ClO4 in methylene chloride was charged in a 100 ml-volume pressure bottle whose atmosphere had been replaced with nitrogen. After removing the methylene chloride by distillation under reduced pressure, the residue was dried in a high vacuum system (1 mmHg) for 1 hour. Then, 14.3 mg (0.022 mM) of the (+)-5,5'-diamino BINAP as obtained in Example 1 and 20 ml of THF were added thereto, followed by stirring at room temperature for 1 hour to prepare 20 ml of a THF solution containing [Rh((+)-5,5'-diamino BINAP)(nbd)]+ClO4−.

Asymmetric Isomerization Using [Rh((+)-5,5'-Diamino BINAP)(nbd)]+ClO4−

To 20 ml of the above-prepared THF solution of the Rh-phosphine complex was added 40 ml of diethyl geranylamine, and the mixture was heated to 100° C. to effect an asymmetric isomerization reaction as shown by the following scheme. The enamine produced was analyzed with the passage of time by gas chromatography to determine conversions to enamine. The results obtained are shown in Table 1.

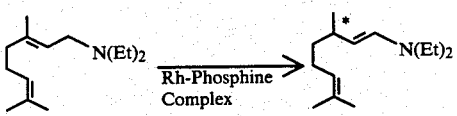

USE EXAMPLE 2

Preparation of [Rh((+)-5,5'-Diacetamide BINAP)(nbd)]+ClO4−

A THF solution containing [Rh((+)-5,5'-diacetamido BINAP)(nbd)]+ClO4− was prepared in the same manner as described in Use Example 1 except for replacing the (+)-5,5'-diamino BINAP as used in Use Example 1 with 15.4 mg (0.022 mM) of the (+)-5,5'-diacetamido BINAP as obtained in Example 2.

Asymmetric Isomerization Using [Rh((+)-5,5'-Diacetamido BINAP)(nbd)]+ClO4−

An asymmetric isomerization reaction was carried out in the same manner as in Use Example 1 except for replacing the THF solution of the Rh-phosphine complex as used in Use Example 1 with 20 ml of the THF solution containing [Rh((+)-5,5'-diacetamido BINAP)(nbd)]+ClO4− as above prepared. The conversions were determined with the passage of time in the same manner as in Use Example 1, and the results obtained are shown in Table 1.

COMPARATIVE USE EXAMPLE

[Rh((+)-BINAP)(nbd)]+ClO4− was prepared in the same manner as described in Use Example 1 except for using unsubstituted (+)-BINAP.

An asymmetric isomerization reaction was carried out in the same manner as in Use Example 1 except for using the thus prepared Rh-phosphine complex to determine conversions with time. The results obtained are shown in Table 1 below.

TABLE 1

| Use Example No. | Rh—Phosphine Complex | Conversion to Enamine (%) | | | |
| --- | --- | --- | --- | --- | --- |
| | | After 1 Hr. | After 3 Hrs. | After 6 Hrs. | After 15 Hrs. |
| 1 | [Rh((+)—5,5'-Diamino BINAP)(nbd)]+ClO4− | 12.3 | 39.6 | 66.8 | 95.9 |
| 2 | [Rh((+)—5,5'-Diacetamido BINAP)(nbd)]+ClO4− | 11.6 | 36.2 | 65.9 | 96.0 |
| Comparative 1 | [Rh((+)—BINAP)(nbd)]+ClO4− | 3.2 | 8.6 | — | 83.0 |

It can be seen from the results of Table 1 above that the phosphine compounds according to the present invention form complexes with a metallic element, e.g., rhodium, ruthenium, palladium, etc., and the resulting complexes exhibit high performances as catalysts for asymmetric syntheses.

While the invention has been described in detail and with reference to specific embodiments thereof, it will be apparent to one skilled in the art that various changes and modifications can be made therein without departing from the spirit and scope thereof.

What is claimed is:

1. A phosphine compound represented by formula:

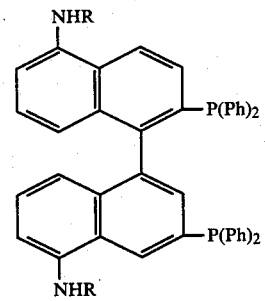

wherein R represents a hydrogen atom or an acetyl group; and Ph represents a phenyl group.

* * * * *